United States Patent [19]

Skuballa et al.

[11] 4,191,823

[45] Mar. 4, 1980

[54] PROCESS FOR THE PREPARATION OF OXAPROSTAGLANDIN INTERMEDIATES

[75] Inventors: Werner Skuballa; Bernd Raduchel; Helmut Vorbrueggen, all of Berlin, Fed. Rep. of Germany

[73] Assignee: Schering Aktiengesellschaft, Berlin and Bergkamen, Fed. Rep. of Germany

[21] Appl. No.: 856,544

[22] Filed: Dec. 1, 1977

[30] Foreign Application Priority Data

Dec. 2, 1976 [DE] Fed. Rep. of Germany ....... 2655004

[51] Int. Cl.$^2$ ............................................. C07D 307/83
[52] U.S. Cl. ............................... 542/426; 260/343.3 P; 260/946
[58] Field of Search ......................... 260/946, 343.3 P; 542/426

[56] References Cited

U.S. PATENT DOCUMENTS

| | | | |
|---|---|---|---|
| 4,055,602 | 10/1977 | Nelson | 260/946 X |
| 4,059,587 | 11/1977 | Smith et al. | 260/946 X |

*Primary Examiner*—Arthur P. Demers
*Attorney, Agent, or Firm*—Millen & White

[57] ABSTRACT

In a process for the preparation of an oxaprostaglandin intermediate of the formula

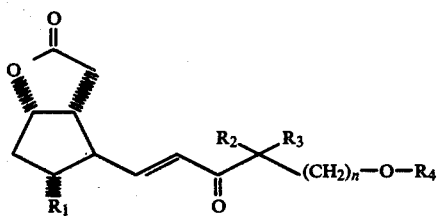

wherein $R_1$ is hydrogen, alkyl, or a free or functionally modified hydroxy group;
$R_2$ and $R_3$ are the same or different, and each is hydrogen, halogen or alkyl;
$R_4$ is alkyl or optionally substituted aryl; and
n is 0, 1, 2 or 3;

which comprises reacting an aldehyde of the formula

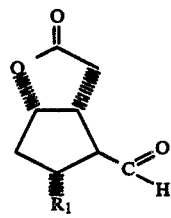

wherein $R_1$ is as defined above with an anion of the formula

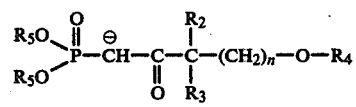

wherein
n, $R_2$, $R_3$ and $R_4$ are as defined above; and
$R_5$ is alkyl;
an improvement is provided wherein the anion is added to the reaction medium in a form which consists essentially of its crystalline alkali metal salt of the formula

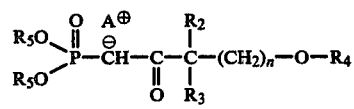

wherein A is an alkali metal atom.

10 Claims, No Drawings

PROCESS FOR THE PREPARATION OF OXAPROSTAGLANDIN INTERMEDIATES

BACKGROUND OF THE INVENTION

This invention relates to a novel process for preparing oxaprostaglandin intermediates.

The oxaprostaglandins prepared by the process of this invention are known compounds of very high pharmacological effectiveness. For example, 16-aryloxy-prostaglandin $F_{2\alpha}$ is commercially available as a highly active luteolytic for animals under the tradename "Equimate".

The synthesis of such oxaprostagladins is described in DOS's [German Unexamined Laid-Open Applications] Nos. 2,223,365, 2,322,673 and 2,606,051. These references disclose methods wherein suitable phenoxypropyl phosphonate solutions are first reacted at temperatures of $-78°$ C. with a butyllithium solution and/or with a NaH suspension under ice cooling conditions. This produces in situ a reactant of the basic formula

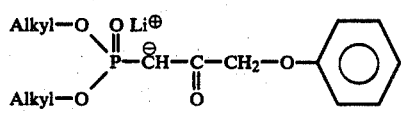

Subsequently, the appropriate aldehyde

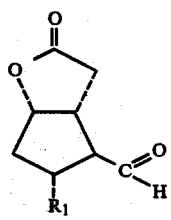

is introduced into this mixture. $R_1$ is H, alkyl, OH or functionally modified OH. After the latter has been worked up, the desired ketone of basic formula

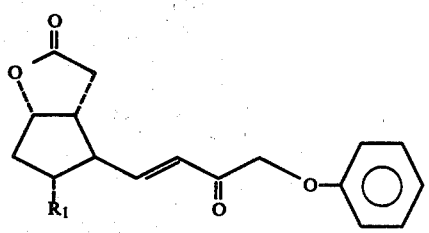

is obtained in yields of 10–40%. Even when the reaction is most carefully controlled, it is impossible to obtain reproducible yields since the reaction is carried out in situ. Thus, undesirable and uncontrollable secondary reactions occur, such as, for example, the splitting-off of the blocking group $R_1$ when a minor excess of alkali is present.

SUMMARY OF THE INVENTION

It is, therefore, an object of the present invention to provide a process for the production of oxaprostaglandin intermediates which can be conducted at room temperature and which produces very satisfactory, reproducible yields, whereby the process can also be used on an industrial scale.

Upon further study of the specification and appended claims, further objects and advantages of this invention will become apparent to those skilled in the art.

It has now been found that the desired oxaprostaglandin intermediates can be obtained at room temperature in reproducible high yields, such as about 87%, by not forming the anion of the phosphonate in situ, but instead isolating this anion as a crystalline compound in the form of its alkali melt salt and thereafter reacting this salt with equimolar quantities of the aldehyde.

Thus, in a process aspect, this invention provides an improvement in a process for the preparation of oxaprostaglandin intermediates of formula I

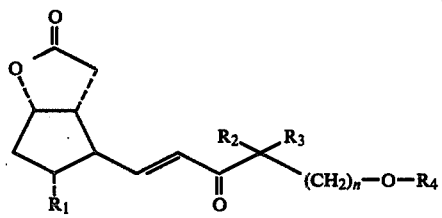

wherein
$R_1$ is hydrogen, alkyl, or a free or functionally modified hydroxy group;
$R_2$ and $R_3$ are the same or different and each is hydrogen, halogen or alkyl;
$R_4$ is alkyl or optionally substituted aryl; and
$n$ is 0, 1, 2 or 3;
the process comprising reacting an aldehyde of formula II

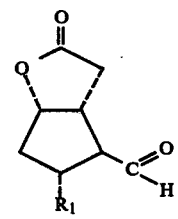

wherein $R_1$ is as defined above, with an anion of formula III

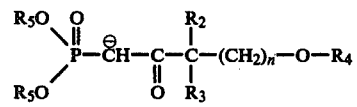

wherein
$n$, $R_2$, $R_3$ and $R_4$ are as defined above; and
$R_5$ is alkyl;
and the improvement being that the anion of formula III is added to the reaction medium in a form which consists essentially of its crystalline alkali metal salt of formula IV

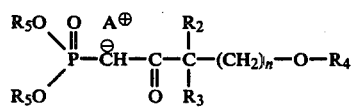

wherein A is an alkali metal atom.

In other reactions between aldehydes of the type represented by formula II and phosphonates different from those used in this invention, the latter have been employed in the form of alkali metal salts. (J. Org. Chem., 38, 1250 (1973); and Chem. Lett., 211 (1976)). However, in such prior art uses of the alkali metal salts, there was no significant increase in reproducibility and size of the yield of the 16-substituted prostaglandin $F_{2\alpha}$, as compared to the results when in situ formation of the phosphate was employed.

DETAILED DISCUSSION

Suitable alkyl groups for $R_1$, $R_2$, $R_3$, $R_4$ and $R_5$ include straight chain and branched alkyl residues of 1–5 carbon atoms such as, for example, methyl, ethyl, propyl, isopropyl, butyl, isobutyl, tert-butyl, and pentyl. The methyl and ethyl groups are preferred.

The hydroxy group $R_1$ can be functionally modified, for example by etherification or esterification. Suitable ether and acyl residues are fully conventional and well known to persons skilled in the art. Preferred are ether residues which can be readily split off, e.g., the tetrahydropyranyl, tetrahydrofuranyl, α-ethoxyethyl, trimethylsilyl, dimethyl-tert-butylsilyl, and tri-p-benzylsilyl residues. Examples of suitable acyl residues include acetyl, propionyl, butyryl, p-phenylbenzoyl, and benzoyl.

Especially suitable as the alkali metal cation A are $Li^+$ and $Na^+$, preferably lithium.

Suitable atoms for $R_2$ and $R_3$ include fluorine and chlorine, fluorine being preferred.

Suitable aryl groups for $R_4$ include those having 6–10 carbon atoms, i.e., phenyl and naphthyl. When $R_4$ is aryl, it can be optionally mono- or trisubstituted by halogen, trifluoromethyl, hydroxy, $C_{6-10}$ aryl, $C_{1-4}$ alkyl and/or $C_{1-4}$ alkoxy. Preferred substituents are halogen, especially chlorine, $C_{1-3}$ alkoxy or $C_{1-3}$ alkyl, particularly methoxy or methyl, and/or triflluoromethyl. Especially preferred are those $R_4$ groups having an unsubstituted benzene nucleus or one which is monosubstituted by chlorine, fluorine or trifluoromethyl.

The reaction of the aldehyde with the alkali metal phosphonate salt takes place suitably in the presence of an inert gas atmosphere, such as, for example, nitrogen and argon, at temperatures of $-70°-+80°$ C., preferably at room temperature, in an inert solvent, e.g., ether, methylene chloride, THF, glyme, dioxane, chloroform, hexane, benzene and others.

The pressure employed during the reaction is not critical and atmospheric pressure is suitable. It is preferred that stoichiometric amounts of the aldehyde and the alkali metal salt be employed. Typical reaction times are 15–240 minutes, preferably 30–90 minutes. The order and rates of addition of the two reactants are not critical but typically the crystalline alkali metal salt is added to the reaction medium containing the aldehyde. All conditions and steps not explicity mentioned herein, such as the subsequent work-up requited to isolate the oxaprostaglandin intermediate product, are fully conventional and, for example, are described in the above-mentioned DOS's Nos. 2,223,365, 2,322,673 and 2,606,051, whose disclosures are incorporated by reference herein.

The alkali metal salts of formula IV are prepared according to methods well known to those skilled in the art, for example by reacting equimolar amounts of the appropriate phosphonate and butyllithium under an inert gas atmosphere (see Example 1 herein.) This reaction takes place between $-70°-+80°$ C., preferably at room temperature, in inert solvents, e.g., pentane, hexane, benzene, toluene, ether, dioxane, and others. (See also, "The Synthesis of Prostaglandins", Abhijit Mitra, John Wiley & Sons (1977), Chapter 19, especially pages 388–391).

The aldehydes of formula II are well known and can also be prepared conventionally. (See also the Mitra reference cited above and those cited in Examples 1 and 2 herein).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

(1S,5R,6R,7R)-6-[(E)-3-Oxo-4-phenoxy-1-butenyl]-7-benzoyloxy-2-oxabicyclo[3,3,0]octan-3-one A solution of 548 mg. of (1S,5R,6R,7R)-6-formyl-7-benzoyloxy-2-oxabicyclo[3,3,0]octan-3-one [J. Amer. Chem. Soc. 96: 5865 (1974)] in 20 ml. of absolute tetrahydrofuran is combined with 581 mg. of the lithium salt of dimethyl-2-oxo-3-phenoxypropyl phosphonate, and the mixture is agitated for 1.5 hours at room temperature under argon. The mixture is then combined with 0.3 ml. of glacial acetic acid, concentrated under vacuum, mixed with 100 ml. of methylene chloride, and extracted with 10 ml. of 5% sodium bicarbonate solution and twice with respectively 10 ml. of water. The product is dried with magnesium sulfate, evaporated under vacuum, and the residue of the evaporation is recrystallized from methylene chloride-isopropyl ether, thus obtaining 710 mg. of the title compound as colorless crystals (yield: 87.5% of theory).

Melting point: 132° C.

The lithium salt of dimethyl-2-oxo-3-phenoxypropyl phosphonate is produced as follows:

At 5° C. and under an argon atmosphere, a mixture of 52.6 ml. of 1.2-molar butyllithium solution in hexane and 150 ml. of hexane are added dropwise to a solution of 16.3 g. of dimethyl-2-oxo-3-phenoxypropyl phosphonate in 430 ml. of absolute ether. A white precipitate is thus obtained; the mixture is stirred for 10 minutes. Vacuum-filtering yields 14.1 g. of the lithium salt as a colorless, crystalline powder.

Melting point: 184° C.

EXAMPLE 2

(1S,5R,6R)-6-[(E)-3-Oxo-4-phenoxy-1-butenyl]-2-oxabicyclo[3,3,0]octan-3-one

A solution of 7.06 g. of (1S,5R,6S)-6-formyl-2-oxabicyclo[3,3,0]octan-3-one [E.J. Corey et al., J. Org. Chem. 39: 256 (1974)] in 450 ml. of absolute tetrahydrofuran is combined with 13.3 g. of the lithium salt of dimethyl-2-oxo-3-phenoxypropyl phosphonate (preparation: see Example 1). The mixture is stirred at room temperature under argon for 2 hours, then neutralized with glacial acetic acid, concentrated under vacuum, combined with 300 ml. of methylene chloride, and the mixture is extracted with 30 ml. of 5% sodium bicarbonate solution and then twice with respectively 30 ml. of water, dried with magnesium sulfate, and evaporated under vacuum. Recrystallization of the residue from isopropanol yields 11.0 g. (84.5% of theory) of the title compound in the form of colorless crystals.

Melting point: 91° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of an oxaprostaglandin intermediate of the formula

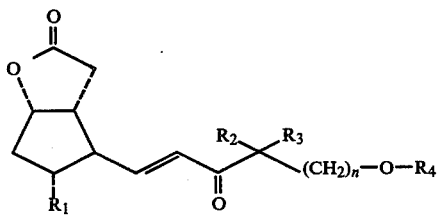

wherein
R₁ is hydrogen, alkyl, or a free or functionally modified hydroxy group;
R₂ and R₃, are the same or different and each is hydrogen, halogen or alkyl;
R₄ is alkyl or optionally substituted aryl; and
n is 0, 1, 2 or 3;
which comprises reacting an aldehyde of the formula

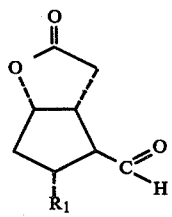

wherein R₁ is as defined above with an anion of the formula

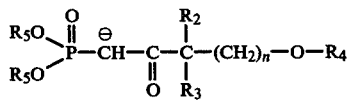

wherein
n, R₂, R₃ and R₄ are as defined above; and
R₅ is alkyl;
the improvement wherein the anion is added to the reaction medium in a form which consists essentially of its crystalline alkali metal salt of the formula

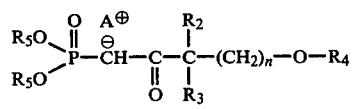

wherein A is an alkali metal atom.

2. The improvement of claim 1 wherein A is Li.

3. The improved process of claim 1 wherein a stoichiometric amount of the alkali metal salt is added to the aldehyde during the reaction.

4. The improved process of claim 1 wherein the reaction is carried out at room temperature.

5. A process for preparing an oxaprostaglandin intermediate of the formula

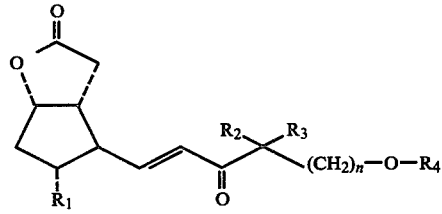

wherein
R₁ is hydrogen, alkyl, or a free or functionally modified hydroxy group;
R₂ and R₃, are the same or different and each is hydrogen, halogen or alkayl;
R₄ is alkyl or optionally substituted aryl; and
n is 0, 1, 2 or 3;
which consists essentially of reacting an aldehyde of the formula

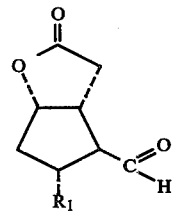

wherein R₁ is as defined above with a previously isolated alkali metal salt of the formula

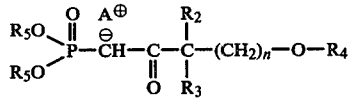

wherein
n, R₂, R₃ and R₄ are as defined above;
A⊕ is an alkali metal cation; and
R₅ is alkyl.

6. The improvement of claim 5 wherein A is Li.

7. The improved process of claim 5 wherein a stoichiometric amount of the alkali metal salt is added to the aldehyde during the reaction.

8. The improved process of claim 5 wherein the reaction is carried out at room temperature.

9. A crystalline alkali metal phosphonate salt of the formula

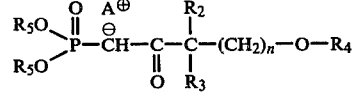

wherein
A is an alkali metal atom;
R₂ and R₃, are the same or different and each is hydrogen, halogen or alkyl;
R₄ is alkyl or optionally substituted aryl;
R₅ is alkyl; and
n is 0, 1, 2 or 3.

10. The salt of claim 9, wherein A is Li.

* * * * *